United States Patent [19]

Gouge et al.

[11] Patent Number: 5,330,047
[45] Date of Patent: Jul. 19, 1994

[54] PACKAGING FOR AGRICHEMICALS

[75] Inventors: Samuel T. Gouge, Raleigh, N.C.; Steven F. McEvoy, Jacksonville, Fla.; Glenn C. Knudsen; Leonard E. Hodakowski, both of Raleigh, N.C.

[73] Assignee: Rhone-Poulenc Inc., Research Triangle Park, N.C.

[21] Appl. No.: 20,506

[22] Filed: Feb. 22, 1993

Related U.S. Application Data

[63] Continuation-in-part of Ser. No. 874,608, Apr. 27, 1992, abandoned.

[51] Int. Cl.$^5$ .............................................. B65D 85/82
[52] U.S. Cl. .................... 206/205; 206/484; 206/524.7
[58] Field of Search ............... 206/D5, 204, 205, 219, 206/524.1, 524.6, 524.7, 525, 527, 568; 71/DIG. 1; 252/315.1; 424/409, 412; 514/801, 812

[56] References Cited

U.S. PATENT DOCUMENTS 3,695,989 10/1972 Albert .
3,892,905 7/1975 Albert .
4,681,228 7/1987 Kerry et al. ..................... 206/524.7
4,874,656 10/1989 Rantanen ........................ 206/524.2

FOREIGN PATENT DOCUMENTS 8912587 12/1989 PCT Int'l Appl. ............. 206/524.7
0922317 3/1963 United Kingdom ............ 206/524.7

Primary Examiner—Jimmy G. Foster
Attorney, Agent, or Firm—James G. Passe'

[57] ABSTRACT

The present invention relates to a containerization system comprising at least one inner water soluble bag located within an outer water insoluble bag. The inner water soluble bag contains an agrichemical that does not substantially dissolve the bag. The outer water insoluble bag is flexible and collapsible and has a low stretchability; it may be made of polyester or laminated polypropylene-polethylene 14 Claims, 1 Drawing Sheet

PACKAGING FOR AGRICHEMICALS

This application is a continuation-in-part of U.S. Ser. No. 07/874,608 filed on Apr. 27, 1992, abandoned.

BACKGROUND OF THE INVENTION

I. Field of the invention

The invention relates to a containerization system and to containers which are particularly suitable for storing, packaging and transporting fluid agricultural chemical compounds, such as pesticides and concentrates thereof.

II. Discussion of the Prior Art

At present, most hazardous and toxic liquids are stored in metal drums or, where smaller quantities are involved, in plastic containers. Hazardous compounds, especially agricultural chemical compounds (agrichemicals), are formulated in various compositions.

The expression toxic or hazardous compounds as used herein means an industrial chemical or agrichemical composition, which, if released in the quantity or concentration normally in storage and shipping containers, may cause damage to the environment or be injurious to a person contacted by it.

Agrichemical compositions in liquid form, particularly in the form of concentrates, are most convenient for farmers because of the relative ease with which they can be handled. There are, nevertheless, difficulties in handling such liquid compositions. There is a danger of spillage or leakage if holes develop in containers that are accidentally dropped and thereby crack or fail. Containers have been developed which possess great resistance to impact and shock. While such containers are secure under normal storage and handling conditions, in the event of an accident, for example during transporting, there remains an appreciable risk of spillage or leakage with rapid loss of liquid. Leakage of toxic and hazardous chemicals can create damage to the environment.

The chemical and packaging industries have long sought a secure container which provides sufficient safeguard for those handling it, such as farmers and transporters, as well as adequate protection for the environment.

It is known, for example, to package agrichemicals in soluble bags or sachets made from water soluble films. While considerable effort has been made and success achieved in improving the strength of such bags, there still remains some relative fragility with such bags resulting from sudden strong impact, for example from dropping.

When designing novel containers for protecting objects having a degree of fragility, rigid materials such as rigid polymers are the construction materials of choice despite the high cost and other problems compared with many flexible polymers. One solution for this problem is exemplified in patent application WO 89/12590 where a water soluble bag containing a liquid agrichemical composition is encased in a novel outer container made of a rigid or semi-rigid polymer such as polypropylene. In its working example, the application describes a container wherein the outer container comprises a rigid body-part which contains the inner bag, i.e. the area within which the bag can move, and the shock absorbing rigid part separated from the body part by means of shoulder, or shock absorbing strips wherein the inner bag cannot move and/or deform completely. In other words, a bag part which is actually the outer container and another added shock absorbing part which is not part of the outside container. Currently, there is such a product available commercially in France called Geludose (Ciba-Geigy) which is a water soluble bag which is stored in a rigid polymeric container. Problems do exist with these types of containers. An external rigid container may break under violent shock and the broken container may have edges which may cut the water soluble bag which is inside of it. Also the lids may become dislodged when the seals are not complete. Even further, because of the complex invention design required for rigid materials, the cost of such product tends to be quite high.

An object of the instant invention is to provide a new containerization system to contain agrichemicals which is safe for everybody.

Another object of the instant invention is to provide a new containerization system to contain agrichemicals which is easy for the farmer to manipulate.

Another object of the instant invention is to provide a new containerization system to contain agrichemicals which is as much condensed as possible, using the least amount of space.

Another object of the instant invention is to provide a new containerization system to contain agrichemicals which is easy to open, easy to manufacture (and thus cheap), and which has a good shock absorption, that is to say, which has a good resistance to shock such as impact and blows.

Another object of the instant invention is to provide a new containerization system to contain agrichemicals which is stable both at high and low temperature.

Another object of the instant invention is to provide a new containerization system and/or a new method to contain agrichemicals which diminishes the risks of pollution.

A further object of the present invention is to provide a containerization system which has no lids, and is easier and cheaper to manufacture and has no problem of lids coming off.

A further object of the present invention is to provide a new containerization system for agrichemicals which reduces the waste disposal of contaminated containers and overpacks.

A further object of the present invention is to provide a new containerization system for agrichemicals which allows very efficient packing and storing due to flexible, optionally flat bags.

An object of the invention is to avoid the risk of spill or pollution and to increase the safety of water soluble packaging of agrichemicals.

Other objects of the invention will better appear from the following description.

SUMMARY OF THE INVENTION

It has surprisingly been found that flexible outer containers can, under proper circumstances and conditions, provide protection to soluble bags. The present invention specifically relates to a containerization system comprising a cold water soluble inner bag containing an agrichemical composition, the said inner bag being contained in an outer bag made of a material which is in the form of a flexible and sealed (preferably heat sealed) polymeric film and is insoluble both in the composition (if liquid or gel) contained in the inner bag and in the solvent which may be comprised in the agrichemical composition contained in the inner bag, the polymeric film having a low stretchability.

Furthermore, the surface of the area delimited by the external largest outline of the inner bag when inside the outer bag should be at least 5 % less than the surface area delimited by the external largest outline of the effectively containing part of the outer bag when containing the inner bag.

The agrochemical composition which is contained in the inner bag of the invention may be solid, or preferably fluid. A solid composition may in the form of powder, dust, granules. By fluid composition, it is meant a composition which may be in form of a liquid or a gel, or also of a solid such as powders or dusts or granules, provided that this solid can deform or even flow easily. However, the gels are preferred in this invention.

Another advantage of the flexible bags of the invention is that they have no parts able to damage other neighboring bags.

Another advantage of the flexible bags of the invention is that they have no lids which may come off due to possibly weak seals.

By polymeric film having a low stretchability, it is meant a film whose elongation at break is less than 100%, preferably less than 30%.

Due to their complete flexibility, the water insoluble bags in this invention may collapse when void. This is especially advantageous by creating less garbage for land filling than known rigid or semi-rigid outer container.

The objects of the invention can be achieved in full or in part by means of the invention.

DETAILED DESCRIPTION OF THE INVENTION

Figure 1:
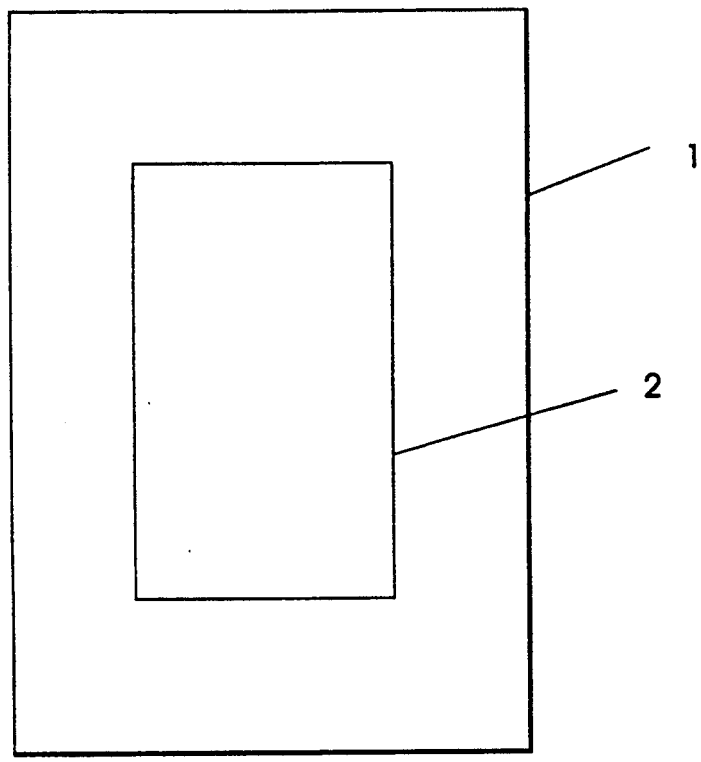
FIG. 1 is a depiction of an outer polymeric bag (1) having an inner water soluble bag (2), wherein the surface area of the inner bag is at least 5% less than that of the outer bag. The bag is free to move inside the outer bag, not being bound thereto.

The containerization system of the present invention comprises one inner water soluble bag containing an agrochemical, more preferably a non-aqueous agrochemical.

The containerization system further comprises an outer water insoluble bag containing the inner bag and its content, and optionally air.

This outer bag is made of a fully flexible film having a thickness of 20 to 500 microns, preferably 30 to 100 microns. By the words fully flexible, it is meant a film which is collapsible and/or may deform completely without effort.

As already said, the outer bag is insoluble in the fluid or the solvent of the fluid of the composition contained in the inner bag.

A preferred polymeric material constituting the outer bag is the polypropylene or the polyethylene, or still more preferably a laminated film made of a first layer of polypropylene and a second layer of polyethylene. This laminated film is preferred because it has both good solvent resistant properties and good heat sealability.

Another preferred material for the outer water insoluble bag of the invention is polyester, advantageously polyethyleneglycol terephtalate.

The agrochemical composition of the invention and the wall of the inner bag it contacts are chosen so that the agrochemical composition does not substantially dissolve the wall of the bag and does not substantially permeate through it. By this it is meant that the dissolution and permeation are each independently less than 5% more preferably less than 1% and most preferably less than 0.5% of the total weight of the bag.

The agrochemical compositions used in this invention are concentrated compositions which are supposed to be diluted with water in a spray tank before use and spraying by the farmer.

The agrochemical compositions which may be used in this invention and which may be contained in the outer or the inner container may be in different physical forms.

They may be in the form of a solid such as powders, preferably water wettable powders, or granules, preferably water dispersible granules.

The agrochemical compositions of this invention may be also in the form of a (preferably non-aqueous) liquid, such as a solution or a dispersion or an emulsion in an organic solvent; this liquid may be more or less viscous; it may be a very fluid liquid such as a liquid having a Brookfield viscosity between 100 and 1000 centipoise, or it may be a viscous liquid, such as a liquid having a Brookfield viscosity from 1000 up to 30000 centipoise (Measurements of viscosities in this specification are made with a Brookfield viscosimeter at 23° C. with a flat plate rotating at 20revolutions per minute).

A further advantageous physical form of the agrochemical compositions of this invention is the form of an organic gel.

Gels which are of particular interest in this invention are organic gels which have viscosities of 600 to 30,000 centipoise, preferably 1,000 to 12,000 centipoise, and still more preferably 1,000 to 5,000 centipoise.

Another feature of the instant invention is an insecticidal composition and insecticidal unit wherein the storage modulus (G' measured as hereafter defined, under speed of oscillations of 1 rd/s=radian per seconde) is in the range of 1 to 10000 Pascal, preferably 10 to 5000 Pascal.

The gel material which is used in this invention is essentially a material which has a phase difference phi between the controlled shear stress and the resulting shear strain such that tg(phi) is less than or equal to 1.5, preferably less than or equal to 1.2. Tg(phi) is the tangent of the phi angle (or phase difference). The measurement of phi is made by means of a dynamic rheometer. Dynamic rheometers which are appropriate to measure phi are known and available commercially. They usually have a flat fixed plate and a rotating cone or plate, or a so-called couette measuring system. Other mechanical systems are also available. Generally the choice of one system or another is made according to the recommendations of the seller of the rheometer, and is adapted to the kind of compound, gel or liquid, which is tested. The particular choice of a specific type of rheometer is something well known by one skilled in the art of rheology. A rotating plate over another plate or a cone rotating over a plate are often more appropriate when a gel or a viscous liquid is tested. When two kinds of system for the rheometer are possible, similar values of phi are actually measured. The cone (or the plate or the couette) is caused to rotate by means of a controlled speed motor; the rotation is a sinusoidal one, i.e., the strain and the angular displacement change as a sine function with time. Tg(phi) is equal to the ratio G"/G', wherein: G' is the storage modulus (represents the behaviour of a perfect solid); G" is the loss modulus (represents the behaviour of a perfect liquid). G' and G" are expressed in Pascal for a given rotational speed (radian per second).

G' and G", and thus tg(phi), may depend on the amplitude of the oscillations (percentage of strain) of the rheometer; however, there is generally a so-called viscoelastic plateau whereby the values G' and G" of a gel do not depend substantially on the said amplitude; this means that in the conditions of the test under the viscoelastic plateau the structure of the gel is maintained and no destruction of the gel into a liquid happens. Of course, the measurement of G' and G" of a gel is made under the conditions of this viscoelastic plateau, just because it corresponds to the normal gel structure which is precisely what is tested.

G' and G", and thus tg(phi), may also depend on the speed of the oscillations (time to reach the chosen percentage of strain; expressed as radian per seconde) of the rheometer; however, when the gel is well structured, there is not so much variation from one speed to another. In order to have a reasonable measurement of the properties of a gel, it is generally preferred to operate in conditions whereby the gel is not too much stressed, that is to say at speed such as 1 rd/s. Of course, measurements at higher speed may also be made.

It is known that a gel is generally a colloid in which the dispersed phase has combined with the continuous phase to produce a viscous, jelly-like product; it is also a dispersed system consisting typically of a high molecular weight compound or aggregate of small particles in very close association with a liquid. The gels used in this invention have basically an organic continuous phase. In contrast, most of the existing materials/gels are water-based and have an aqueous continuous phase. Furthermore, the gels used in this invention have essentially one physical phase, at least as can be seen when visually observed. Preferred gels in this invention are also gels which can be divided by cutting and whose cut parts are able to merge together by simple juxtaposition.

When the fluid agrochemical composition contained in the inner bag of the invention is not a gel, it may be a material which has a phase difference phi between the controlled shear stress and the resulting shear strain, such that tg(phi) is greater than or equal to 1.5. More generally, it is then a liquid which has a phase difference phi between the controlled shear stress and the resulting shear strain, such that tg(phi) is greater than or equal to 5. Such liquid have generally a viscosity less than 12000 cps.

The non aqueous agrochemical compositions which are used in this invention are essentially materials having a low water content, generally less than 5% (by weight), preferably less than 3%, more preferably less than 1%.

The choice of the particular physical form of the agrichemicals used in this invention depends on the particular agrichemicals which are involved.

The following features, alone or in combination, constitute preferred features of the invention:

According to one feature, the hazardous product is preferably an agrochemical, or more precisely a plant protection agents (including pesticides, such as insecticides, fungicides, herbicides, acaricides or nematocides) or plant growth regulators or plant nutrients, or an adjuvant for the activity for plants as activity promoters including penetrating agents, synergists, antidotes, sticking agents, spreaders, activators, compatibility agents; adjuvants for the water soluble bags as plasticizers.

The invention is not limited to some specific agrichemicals; a list of many agrichemicals which can be used in the poly-bag system of the invention includes:

fungicides such as triadimefon, tebuconazole, prochloraz, triforine, tridemorph, propiconazole, pirimicarb, iprodione, metalaxyl, bitertanol, iprobenfos, flusilazol, fosetyl, propyzamide, chlorothalonil, dichlone, mancozeb, anthraquinone, maneb, vinclozolin, fenarimol, bendiocarb, captafol, benalaxyl, thiram;

herbicides (or defoliants) such as quizalofop and its derivatives, acetochlor, metolachlor, imazapur and imazapyr, glyphosate and gluphosinate, butachlor, acifluorfen, oxyfluorfen, butralin, fluazifop-butyl, bifenox, bromoxynil, ioxynil, diflufenican, phenmedipham, desmedipham, oxadiazon, mecoprop, MCPA, MCPB, linuron, isoproturon, framprop and its derivatives, ethofumesate, diallate, carbetamide, alachlor, metsulfuron, chlorsulfuron, chlorpyralid, 2,4-D, tribufos, triclopyr, diclofop-methyl, sethoxydim, pendimethalin, trifluralin, ametryn, chloramben, amitrole, asulam, dicamba, bentazone, atrazine, cyanazine, thiobencarb, prometryn, 2-(2-chlorobenzyl)-4,4-dimethyl-1,2-oxazolidin-3-one, fluometuron, napropamide, paraquat, bentazole, molinate, propachlor, imazaquin, metribuzin, tebuthiuron, oryzalin;

insecticides or nematicides such as ebufos, carbosulfan, amitraz, vamidothion, ethion, triazophos, propoxur, phosalone, permethrin, cypermethrin, parathion, methylparathion, diazinon, methomyl, malathion, lindane, fenvalerate, ethoprophos, endrin, endosulfan, dimethoate, dieldrin, dicrotophos, dichlorprop, dichlorvos, azinphos and its derivatives, aldrin, cyfluthrin, deltamethrin, disulfoton, chlordimeform, chlorpyrifos, carbaryl, dicofol, thiodicarb, propargite, demeton, phosalone; and plant growth regulators such as gibberellic acid, ethrel or ethephon, cycocel, chlormequat, ethephon, mepiquat.

According to another feature, the bags of the invention are filled to at least 60% of capacity with the agrochemical composition (and the inner bag if any), more preferably to at least 70% of capacity, still more preferably 80 to 99% of capacity and most preferably 85 to 95% of capacity. The outer bag is preferably not filled to complete capacity because the unused capacity gives the shock resistance, i.e., resistance to breakage when dropped, transported or stored. This unused capacity may or may not contain air or inert gas. An absence of air or inert gas in the unused capacity further improves shock resistance. However in deciding how much unused capacity, or absence of air or inert gas, to provide, the advantages of shock resistance must be balanced against the need, if any, for shock resistance and the cost of providing shock resistance. For example, if the outer bag is stored and/or transported in a shock absorbing container, then it may not be as helpful to provide this unused capacity.

Also, the capacity to which the outer bag is filled, and whether the unused capacity does or does not contain air is affected by whether it is desired to have the bag sink or float.

When the bag is filled with solids, the capacity is relative to bulk volume of the solids, not the actual particle volume of the solids.

In practice the agrochemical compositions used in the instant invention generally comprises the active ingredient-s) in association with other ingredients, for example surfactants, dispersants, thickeners, antifoaming, antifreezing, gelled agents or gelling agents.

According to another feature the inner bags used in this invention are made of a polymeric water soluble film, more precisely a cold water soluble film. Cold water soluble means soluble in water at temperature less than 35° C., generally between 5° C. and 35° C. The thickness of this film is generally between 10 and 500 microns, preferably between 20 and 100 microns.

The chemical nature of the enveloping film constituting the inner bag can vary quite widely. Suitable materials are water soluble (or possibly water dispersible) materials which are insoluble in the organic solvents used to dissolve or disperse the agrochemical active ingredient. Specific suitable materials include polyethylene oxide, such as polyethylene glycol; starch and modified starch ; alkyl and hydroxyalkylcellulose, such as hydroxymethylcellulose, hydroxyethylcellulose, hydroxypropyl cellulose; carboxymethylcellulose; polyvinylethers such as poly methyl vinylether or poly(2-methoxyethoxyethylene); poly(2,4-dimethyl-6-triazinylethylene; poly(3-morpholinyl ethylene); poly(N-1,2,4-triazolylethylene);poly(vinylsulfonicacid); polyanhydrides; low molecular weight melamine-formaldehyde resins; low molecular weight urea-formaldehyde resins; poly(2-hydroxyethyl methacrylate); polyacrylic acid and its homologs. Preferably the enveloping film comprises or is made from polyvinylalcohol (PVA). PVA is generally partially or fully alcoholysed or hydrolysed e.g. 40-100%, preferably 80-99% alcoholysed or hydrolysed, polyvinyl acetate (or other ester) film; copolymers or other derivatives of such polymers can also be used.

Preferred materials for constituting the bags in this invention are polyethylene oxide or methylcellulose, or polyvinylalcohol. When polyvinylalcohol is used, it is advantageously a 40-100% alcoholysed or hydrolysed, preferably 80-99% alcoholysed or hydrolysed, polyvinyl acetate film.

The polymeric material constituting the wall of the inner bag may be dissolved in similar conditions in cold water (cold means less than 35° C.).

The inner bag of the containerization system of the invention may be opened preferably through an easy tearing tab. Optionally, the bag may have a notch permitting to easier tear off the tab. An advantage of polyester water insoluble bag is to permit to tear off the tab more easily than polyolefins water insoluble bags. Thus there is less risk to damage the inner bag when it has to be opened; less risk to damage includes less risk of break and leakage. This is especially important for farmers who, rather often, have wet hands or are wearing groves and may have unsuitable moves causing damage to the bag.

For the same reasons, the water insoluble bags are preferably bags which can be easily resealed. This is easier to make with polyesters films. The resealable part of the bag may have a pressure seal, such as a pressure resealable top, or a so-called zip-lock bag seal; it may be too a zippered top; this resealable top may be unzipped (opened) and rezipped (reclosed). These resealable bags are more environment friendly embodiment of the invention because any spill of agrichemicals in the outer bag at the time the inner bag is opened may be confined inside the outer water insoluble bag.

The preparation or manufacturing of the containerization system of the invention can be done according the known process of preparation or manufacturing of water soluble bags. As a practical manner, the first bag (that is to say the inner bag, or inner bags if more than one) is prepared from a water soluble film, optionally by partial sealing or heat sealing. Then it is filled with an agrochemical composition and the bag(s) is finally closed. Then the second bag (that is to say the outer bag) is prepared in the same way. However it is filled with the first bag previously prepared. This later outer bag is also closed by sealing, optionally heat sealing.

A particular embodiment of the invention is a containerization system which comprises at least one inner cold water soluble bag containing an agrochemical composition, the containerization system further comprising an outer water insoluble bag made of a flexible and sealed (optionally heat sealed) polymeric film.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface area delimitated by the external largest outline of the effectively containing part of the outer bag when containing the inner bag that is to say the inner bag is able to move freely in the outer bag in such a way that if any side of the inner bag comes into close contact with the outer bag, the opposite side of the said inner bag is at a distance from the closest side of the wall of the outer bag which is at least 5% of the distance between the contacting side of the opposite non-contacting side. This allows room for the inner bag to recoil when contact is made from an abrupt impact and in general the inner bag is free to move within the limits of the outer bag.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein the inner bag of the containerization system of the invention may be opened through a tearing tab.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein the inner bag of the containerization system of the invention may be opened through a tearing tab.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface area delimitated by the external largest outline of the effectively containing part of the outer bag when containing the inner bag, and wherein the inner bag of the containerization system of the invention may be opened through a tearing tab.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag, and wherein the inner bag of the containerization system of the invention may be opened through a tearing tab.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and the said water insoluble outer bag comprising a resealable seal or a pressure seal or a zip-lock seal.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and the said water insoluble outer bag comprising a resealable seal or a pressure seal or a zip-lock seal.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface area delimitated by the external largest outline of the effectively containing part of the outer bag when containing the inner bag, and the said water insoluble outer bag comprising a resealable seal or a pressure seal or a zip-lock seal.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag, and the said water insoluble outer bag comprising a resealable seal or a pressure seal or a zip-lock seal.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein the inner bag of the containerization system of the invention may be opened through a tearing tab, and the said water insoluble outer bag comprising a resealable seal or a pressure seal or a zip-lock seal.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein the inner bag of the containerization system of the invention may be opened through a tearing tab, and the said water insoluble outer bag comprising a resealable seal or a pressure seal or a zip-lock seal.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface area delimitated by the external largest outline of the effectively containing part of the outer bag when containing the inner bag, and wherein the inner bag of the containerization system of the invention may be opened through a tearing tab, and the said water insoluble outer bag comprising a resealable seal or a pressure seal or a zip-lock seal.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag, and wherein the inner bag of the containerization system of the invention may be opened through a tearing tab, and the said water insoluble outer bag comprising a resealable seal or a pressure seal or a zip-lock seal.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface area delimitated by the external largest outline of the effectively containing part of the outer bag when containing the inner bag, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein the inner bag of the containerization system of the invention may be opened through a tearing tab, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein the inner bag of the containerization system of the invention may be opened through a tearing tab, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface area delimitated by the external largest outline of the effectively containing part of the outer bag when containing the inner bag, and wherein the inner bag of the containerization system of the invention may be opened through a tearing tab, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag, and wherein the inner bag of the containerization system of the invention may be opened through a tearing tab, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and the said water insoluble outer bag comprising a resealable seal or a pressure seal or a zip-lock seal, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and the said water insoluble outer bag comprising a resealable seal or a pressure seal or a zip-lock seal, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface area delimitated by the external largest outline of the effectively containing part of the outer bag when containing the inner bag, and the said water insoluble outer bag comprising a resealable seal or a pressure seal or a zip-lock seal, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag, and the said water insoluble outer bag comprising a resealable seal or a pressure seal or a zip-lock seal, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein the inner bag of the containerization system of the invention may be opened through a tearing tab, and the said water insoluble outer bag comprising a resealable seal or a pressure seal or a zip-lock seal, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein the inner bag of the containerization system of the invention may be opened through a tearing tab, and the said water insoluble outer bag comprising a resealable seal or a pressure seal or a zip-lock seal, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, and wherein, the surface of the area delimitated by the external largest outline of the inner bag when inside the outer bag is at least 5% less than the surface area delimitated by the external largest outline of the effectively containing part of the outer bag when containing the inner bag, and wherein the inner bag of the containerization system of the invention may be opened through a tearing tab, and the said water insoluble outer bag comprising a resealable seal or a pressure seal or a zip-lock seal, and wherein the polymeric film is collapsible and has an elongation at rupture less than 100%.

Another particular embodiment of the invention is a containerization system which comprises at least one inner cold water soluble bag containing an agrochemical composition, the containerization system further comprising an outer water insoluble bag made of a flexible and sealed (optionally heat sealed) polymeric film, which is insoluble both in the composition (if liquid or gel) contained in the inner bag and in the solvent which may be comprised in the agrochemical composition contained in the inner bag, the polymeric film having a low stretchability, and wherein, the surface of the area delimitated by the external largest outline of the inner bag when inside the outer bag is at least 5% less than the surface area delimitated by the external largest outline of the effectively containing part of the outer bag when containing the inner bag, and wherein the inner bag of the containerization system of the invention may be opened through a tearing tab, and the said water insoluble outer bag comprising a resealable seal or a pressure seal or a zip-lock seal, and wherein the polymeric film is collapsible and has an elongation at rupture less than 100%.

Another particular embodiment of the invention is a containerization system according to anyone of the previous embodiments wherein the agrochemical composition is solid Another particular embodiment of the invention is a containerization system according to anyone of the previous embodiments wherein the agrochemical composition is fluid Another particular embodiment of the invention is a containerization system according to anyone of the previous embodiments wherein the agrochemical composition is a liquid or a gel Another particular embodiment of the invention is a containerization system according to anyone of the previous embodiments wherein the agrochemical composition is a powder or a dust or granules Another particular embodiment of the invention is a containerization system according to anyone of the previous embodiments wherein the polymeric film has an elongation at rupture less than 30%

Another particular embodiment of the invention is a containerization system according to anyone of the previous embodiments wherein the polymeric film is made of polyester Another particular embodiment of the invention is a containerization system according to anyone of the previous embodiments wherein the polymeric film is a laminated film of polypropylene and polyethylene Another particular embodiment of the invention is a containerization system according to anyone of the previous embodiments wherein the polymeric film has a thickness of 20 to 500 microns Another particular embodiment of the invention is a containerization system according to anyone of the previous embodiments wherein the polymeric film has a thickness of 30 to 100 microns Another particular embodiment of the invention is a containerization system according to anyone of the previous embodiments wherein the agrochemical is selected in the group comprising plant protection agents, pesticides, insecticides, fungicides, herbicides, acaricides, nematocides, plant growth regulators, plant nutrients, or an adjuvant for the activity for plants as activity promoters including penetrating agents, synergists, antidotes, sticking agents, spreaders, activators, compatibility agents; adjuvants for the water soluble bags as plasticizers.

Another particular embodiment of the invention is a containerization system according to anyone of the previous embodiments wherein the water soluble polymeric film constituting the inner bag comprises polyethylene oxide or methylcellulose, or polyvinylalcohol.

The following examples are given for illustrative purposes and should not be understood as restricting the invention.

In these examples, the Brookfield viscosity was measured, as previously indicated, with a Brookfield viscosimeter which had a flat plate rotating at 20 revolutions per minute.

In all the following examples, the prepared gels had a tg(phi) of between 0.75 and 1.5. Further information may be found in the following copending applications, the disclosures of which are incorporated herein by reference: U.S. Ser. No. 07/713,681, application of David B. Edwards, William J. Mc Carthy, Leonard E. Hodakowski, Chi-Yu R. Chen, Samuel T. Gouge and Paul J. Weber for "Laminated Bags for containerization of Toxic or Hazardous Materials" filed Jun. 11, 1991; U.S. Ser. No. 07/713,682, application of Samuel T. Gouge, Leonard E. Hodakowski, Paul J. Weber and Chi-Yu R. Chen for "Gel Formulations for Hazardous Products" filed Jun. 11, 1991; U.S. Ser. No. 07/713,701, application of Leonard E. Hodakowski, Chi-Yu R. Chen, Samuel T. Gouge and Paul J. Weber for "Water Dispersible Gel Formulations" filed Jun. 11, 1991; U.S. Ser. No. 07/713,685, application of Leonard E. Hodakowski, Ricky W. Couch, Samuel T. Gouge and Robert C. Ligon for "Gel Formulations" filed Jun. 11, 1991; and U.S. Ser. No. 07/713,683, application of Leonard E. Hodakowski, Chi-Yu R. Chen, Samuel T. Gouge and Paul J. Weber for "Gel Formulations for Use in Toxic or Hazardous Product Containerization Systems" field Jun. 11, 1991.

EXAMPLE 1

A gel was made by stirring and shaking at 50° C. a mixture of the following ingredients until they were each dissolved or dispersed:

| | |
|---|---|
| active ingredient: the herbicide 2,4-D; phenoxy benzoic acid (isooctyl ester): | 64.8% |
| solvent: aromatic solvent with flash point of 65° C.: | 24.2%; |
| adjuvants: | |
| non ionic/sulfonate blended emulsifier: | 4%; |
| calcium alkylbenzene sulfonate: | 1%; |
| mixture of dioctylsulfosuccinate salt and sodium benzoate | 6%. |

During stirring, a dissolution or dispersion appeared, and thereafter gelation. Gelation increased as the mixture cools to about 20° C.

The Brookfield viscosity of the gel was 3000 centipoise. 800 g of this gel were put in a one-liter bag made of a film of PVA (88% hydrolyzed polyvinyl acetate; cold water soluble; thickness: 55 microns). The bag was partially full and had a residual inflatability of 20%. The outline of this bag was 25.4 cm long and 15 cm wide.

This bag was put in an outer bag, or overpack, whose outline was 28 cm long and 16 cm wide.

The outer bag was made of a flexible laminated film made of one layer of polypropylene (outer layer) and one (inner) layer of polyethylene. Both bags were heat sealed.

The bag in the outer bag was dropped repeatedly from 0.79 m above the ground. An average of 36 drops were necessary to obtain failure of the outer bag. Even in this case, the inner bag had no failure.

The bag alone or the bag in a known rigid container had failure with a substantially less number of repeated drops, and the inner bag may be injured.

EXAMPLE 2

Example 1 was repeated except that the outer bag was a polyester bag that had a zip lock opening and closing mechanism.

The bag in the outer bag was dropped repeatedly from 0.79 m above the ground. An average of 32 drops were necessary to obtain failure of the outer bag. Even in this case, the inner bag had no failure.

What is claimed is:

1. A containerization system which comprises at least one inner cold water soluble bag containing an agrochemical composition in an outer water insoluble bag made of a flexible and sealed polymeric film, each bag having a surface area delimited by the external largest outline thereof, wherein the surface area of the inner bag is at least 5% less than the surface area of the outer bag, and wherein the entire outer surface of said inner bag is loosely enclosed by the outer bag such that the inner bag is free to move in the outer bag.

2. A containerization system according to claim 1 wherein the outer bag is insoluble in the composition contained in the inner bag.

3. A containerization system according to claim 1, wherein the polymeric film of the outer bag of the containerization system has an elongation at break of less than 100%.

4. A containerization system according to anyone of claims 1, 2 or 3, wherein the polymeric film is collapsible.

5. A containerization system according to any one of claims 1, 2 or 3, wherein the agrichemical composition is solid.

6. A containerization system according to any one of claims 1, 2 or 3, wherein the agrichemical composition is fluid.

7. A containerization system according to any one of claims 1, 2 or 3, wherein the agrichemical composition is a liquid or a gel.

8. A containerization system according to any one of claims 1, 2 or 3, wherein the agrichemical composition is a powder or a dust or granules.

9. A containerization system according to any one of claims 1, 2 or 3, wherein the polymeric film has an elongation at rupture less than 30%.

10. A containerization system according to anyone of claims 1, 2 or 3, wherein the polymeric film is made of polyester.

11. A containerization system according to anyone of claims 1, 2 or 3, wherein the polymeric film has a thickness of 20 to 500 microns.

12. A containerization system according to claims 1, 2 or 3, wherein the polymeric film has a thickness of 30 to 100 microns.

13. A containerization system according to any one of claims 1, 2 or 3, wherein the agrichemical is selected in the group comprising plant protection agents, pesticides, insecticides, fungicides, herbicides, acaricides, nematicides, plant growth regulators, plant nutrients, or an adjuvant for the activity for plants as activity promoters including penetrating agents, synergists, antidotes, sticking agents, spreaders, activators, compatibility agents; adjuvants for the water soluble bags as plasticizers.

14. A containerization system according to any one of claims 1, 2 or 3, wherein the water soluble polymeric film constituting the inner bag comprises polyethylene oxide or methylcellulose, or polyvinylalcohol.

* * * * *